(12) United States Patent
Senf et al.

(10) Patent No.: US 9,618,487 B2
(45) Date of Patent: Apr. 11, 2017

(54) PREFILLED LIQUID CARTRIDGE FOR THE SUPPLY OF A SAMPLE SEPARATION DEVICE WITH AN OPERATING LIQUID

(71) Applicant: AGILENT TECHNOLOGIES, INC., Loveland, CO (US)

(72) Inventors: Manuela Senf, Waldbronn (DE); Daniela Loraing, Waldbronn (DE); Qi Siegmundt-Pan, Waldbronn (DE)

(73) Assignee: Agilent Technology, Inc., Santa Clara, CA (US)

( * ) Notice: Subject to any disclaimer, the term of this patent is extended or adjusted under 35 U.S.C. 154(b) by 601 days.

(21) Appl. No.: 14/076,147

(22) Filed: Nov. 8, 2013

(65) Prior Publication Data
US 2014/0158615 A1 Jun. 12, 2014

(30) Foreign Application Priority Data
Dec. 11, 2012 (DE) .................. 10 2012 222 828

(51) Int. Cl.
*B01D 15/10* (2006.01)
*B01D 15/18* (2006.01)
(Continued)

(52) U.S. Cl.
CPC ......... *G01N 30/6091* (2013.01); *B01D 15/10* (2013.01); *B01D 15/18* (2013.01);
(Continued)

(58) Field of Classification Search
CPC ........ B01D 15/08; B01D 15/10; B01D 15/22; B01D 15/12; B01D 15/14; B01D 15/18; B01D 17/06; B01L 3/52; B01L 3/523; B01L 3/56; B01L 3/561; B01L 3/563; B01L 3/565; B01L 2200/025; B01L 2200/026; B01L 2200/16; G01N 30/06; G01N 30/26;
(Continued)

(56) References Cited

U.S. PATENT DOCUMENTS 3,767,365 A * 10/1973 Beesley ............ B01D 11/0476
210/658
4,070,284 A * 1/1978 Fujita ..................... B01D 15/08
210/198.2
(Continued)

FOREIGN PATENT DOCUMENTS

WO WO9924137 A1 5/1999
WO WO2008032030 3/2008
(Continued)

OTHER PUBLICATIONS

Office Action mailed Sep. 24, 2013 in German Patent Application No. 102012222828.4.

*Primary Examiner* — Joseph Drodge (57) ABSTRACT

Prefilled liquid cartridge for fluidically connecting to a sample separation device for separating of components of a fluidic sample by using liquid of the liquid cartridge, wherein the liquid cartridge comprises a liquid container which is prefilled with liquid and a liquid removal access provided at the liquid container, adapted to be fluidically coupled with at least one liquid conduit of the sample separation device by only inserting the liquid cartridge in a corresponding liquid cartridge accommodation of the sample separation device.

27 Claims, 2 Drawing Sheets

(51) Int. Cl.
*B01L 3/00* (2006.01)
*G01N 27/26* (2006.01)
*G01N 30/06* (2006.01)
*G01N 30/26* (2006.01)
*G01N 30/60* (2006.01)
*G01N 27/447* (2006.01)
*G01N 30/88* (2006.01)

(52) U.S. Cl.
CPC .............. *B01L 3/523* (2013.01); *G01N 27/26* (2013.01); *G01N 27/44704* (2013.01); *G01N 30/06* (2013.01); *G01N 30/26* (2013.01); *B01L 2200/025* (2013.01); *B01L 2300/044* (2013.01); *G01N 2030/8881* (2013.01)

(58) Field of Classification Search
CPC ....... G01N 30/6091; G01N 2030/8881; G01N 27/00; G01N 27/06; G01N 27/07; G01N 27/26; G01N 27/447; G01N 27/44704; G01N 30/04; G01N 30/16; G01N 30/38; G01N 30/60
USPC .............. 73/61.52, 61.53, 61.55, 61.56, 864, 73/864.21, 864.31, 864.51; 210/198.2, 210/635, 656; 422/70, 501, 502, 547, 549
See application file for complete search history.

(56) References Cited

U.S. PATENT DOCUMENTS

| | | | | | |
|---|---|---|---|---|---|
| 4,228,007 | A | * | 10/1980 | Rausch | B01D 15/206 210/198.3 |
| 5,037,544 | A | * | 8/1991 | Snyder | B01D 15/22 210/198.2 |
| 5,173,192 | A | * | 12/1992 | Shalev | B01D 35/04 210/244 |
| 5,571,720 | A | * | 11/1996 | Grandics | C12M 47/12 210/194 |
| 8,778,155 | B2 | * | 7/2014 | Tsai | G01N 27/44756 204/451 |
| 2002/0155033 | A1 | * | 10/2002 | Strand | B01J 19/0093 422/400 |
| 2005/0092685 | A1 | | 5/2005 | Hilhorst et al. | |
| 2005/0133426 | A1 | | 6/2005 | DeMarco | |
| 2006/0027490 | A1 | * | 2/2006 | DeMarco | G01N 30/88 210/198.2 |
| 2008/0200343 | A1 | * | 8/2008 | Clemens | G01N 27/27 506/9 |
| 2009/0221059 | A1 | * | 9/2009 | Williams | B01L 3/5027 435/287.2 |
| 2010/0291588 | A1 | * | 11/2010 | McDevitt | B01L 3/502715 435/7.2 |
| 2012/0123091 | A1 | * | 5/2012 | Blaschyk | B01D 15/22 530/344 |
| 2012/0264114 | A1 | * | 10/2012 | Wacogne | B01L 3/50273 435/5 |
| 2013/0068946 | A1 | * | 3/2013 | Moskovets | G01N 30/7233 250/288 |
| 2013/0244241 | A1 | * | 9/2013 | Carrera Fabra | C12M 23/42 435/6.12 |

FOREIGN PATENT DOCUMENTS

WO  WO2009016431  2/2009
WO  WO2011018658  2/2011

\* cited by examiner

PREFILLED LIQUID CARTRIDGE FOR THE SUPPLY OF A SAMPLE SEPARATION DEVICE WITH AN OPERATING LIQUID

The present application claims priority under 35 U.S.C. §119(e) from German Patent Application No. 102012222828.4 filed on Dec. 11, 2012 naming Manuela Senf, et al. as inventors. The entire disclosure of German Patent Application No. 102012222828.4 is specifically incorporated herein by reference.

The present invention is related to a prefilled liquid cartridge, a sample separation device, an arrangement and a method.

BACKGROUND

In an HPLC, typically a liquid (mobile phase) is moved through a stationary phase (for example a chromatographic separation column) at a very precisely controlled flow rate (for example in the range from microliters to milliliters per minute) and at a high pressure (typically 20 bar to 1000 bar and beyond, currently up to 2000 bar) at which the compressibility of the liquid is noticeable, to separate single components of a sample liquid which is introduced into the mobile phase. In a flow cell of a liquid chromatography device the detection of the separated fractions of the sample is carried out. For this purpose the fluidic sample is guided by a capillary downstream of the separation column into a container of the flow cell. While the fluidic sample passes the flow cell, a fluorescence measurement of the sample can be executed, whereby the individual fractions of the sample can be identified and quantified respectively.

Such an HPLC system is known from EP 0,309,596 B1 from the same applicant, Agilent Technologies, Inc.

For executing chromatographic separations, different operating liquids, particularly solvents, are necessary. These are filled in open bottles. These bottles are put at the upper side of a liquid chromatography device consisting of multiple modules and are connected to the modules by tubes inserted in the bottles.

In such fluid handling devices the handling of the bottles and tubes is cumbersome for a user because these have to be handled in many cases above shoulder height. Further, because certain solvents are critical for the health, this arrangement of bottles is not hazard-free, because when handling the bottles open at the upper side and tubes above shoulder height, the bottles can be in danger of tipping.

DISCLOSURE

It is an object of the invention to enable the hazard-free and user-friendly handling of operating liquids for operating a sample separation device or the like.

According to an exemplary embodiment of the present invention, a prefilled liquid cartridge for fluidically connecting to a sample separation device or system for separating of components of a fluidic (particularly liquid) sample, using liquid of the liquid cartridge is created, wherein the liquid cartridge comprises a liquid container which is prefilled with liquid and a liquid removal access provided at the liquid container, which is adapted to be fluidically coupled with at least one liquid conduit of the sample separation device only by inserting the liquid cartridge in a corresponding liquid cartridge accommodation of the sample separation device.

According to another exemplary embodiment, a sample separation device or system for separating of components of a fluidic sample using liquid of a liquid cartridge is provided, wherein the sample separation device comprises at least one housing, at least one functional equipment which is arranged at least partially in the at least one housing and is adapted for providing a function in the scope of separating of components of the fluidic sample using liquid of the liquid cartridge, at least one liquid conduit arranged at and/or in the housing for supplying the at least one functional equipment with liquid, and a liquid cartridge accommodation provided at and/or in the at least one housing, which is adapted for accommodating a corresponding prefilled liquid cartridge so that by only inserting the prefilled liquid cartridge in the liquid cartridge accommodation a fluidic coupling between the at least one liquid conduit and the prefilled liquid in the liquid container of the liquid cartridge is formed by a liquid removal access provided at the liquid container.

According to a further exemplary embodiment an arrangement is provided which comprises a sample separation device or system with the above described features for separating of components of a fluidic sample using liquid of a liquid cartridge and this liquid cartridge with the above described features being inserted or insertable in the sample separation device and being prefilled.

According to a further exemplary embodiment, a method for liquid supply of a sample separation device or system for separating of components of a fluidic sample using liquid of a liquid cartridge is created, wherein in the method a liquid cartridge prefilled with liquid is inserted into a liquid cartridge accommodation at and/or in at least one housing of the sample separation device so that by only inserting (i.e. automatically by finishing the inserting) a fluidic coupling between at least one liquid conduit of the sample separation device and the prefilled liquid in a liquid container of the liquid cartridge is formed by a liquid removal access of the liquid cartridge provided at the liquid container, and the liquid is conveyed from the inserted liquid cartridge through a liquid removal access and the at least one liquid conduit to at least one functional equipment of the sample separation device, which is arranged at least partially in the at least one housing of the sample separation device.

According to an exemplary embodiment of the invention, a liquid cartridge is provided which is already prefilled with liquid before initial operation by a user, which can be used as a disposable cartridge to provide operating liquids, for example solvent or the like, to a sample separation device. Such a prefilled liquid cartridge can be connected to a sample separation device by a user starting from an outwardly fluid-tight state, wherein only by executing an insertion motion, a correct fluidic coupling between the inside of the prefilled cartridge on the one hand and a respective fluidic interface of the sample separation device or other sample handling device is established. Thereby, for a user the handling of such a prefilled cartridge and solvents which are required for a sample separation device, is extremely easy. In contrast to conventional systems it is not required any more to fill solvents in containers by hand and connect them to the sample separation device by provisional tube connections. According to embodiments of the invention, a better reproducibility of the measurements can be achieved, because solvents are provided with completely defined, standardized conditions. According to embodiments of the invention, it is also not required any more to handle upwardly open liquid containers over height of the head, because a simple inserting of the prefilled liquid cartridge into a corresponding slot of the sample separation device is adequate to effect the feeding of the operating liquids to the sample separation device. When the prefilled liquid cartridges are formed fluid-tight before initial operation, a contamination with partially health concern solvents or other operating liquids of the sample separation device is not expected any more, even when tipping the liquid cartridges. By the prefilling of the liquid cartridges at factory, easy to handle cartridges can be provided which seem like a black box outwardly and only have to be docked to the sample separation device to allow the supply of the sample separation device with the operating liquid or operating liquids. Thereby sample separation experiments can be operated more error-robust.

In the following, embodiments of the prefilled liquid cartridge, the sample separation device, the arrangement and the method will be described.

According to an embodiment, the liquid container with the liquid can be prefilled fluid-tight (i.e. liquid and/or gas-tight) before a first fluid removal through the liquid removal access. In other words the liquid container can be formed so that the liquid contained in it is completely inaccessible or hermetically sealed inside the liquid container. Only by the first removing of liquid, the fluid-tight protection will be overcome.

According to an embodiment, the liquid container with the liquid can be prefilled sterile and/or aseptic. Thereby a longer storage of the liquid cartridge before a first use is possible. The sterile providing of solvents is advantageous especially when handling sensitive biological samples. Contaminations which can influence the sample separation process negatively can be reliably avoided in this way.

According to an embodiment, the liquid container can be prefilled with a solvent, particularly with an organic and/or inorganic solvent. Such solvents are used in chromatographic separation processes for example, where a gradient of solvent is applied to a sample. Thereby sample material which is immobilized at a liquid chromatography column is detached from the column in fractions and separated thereby. Examples for usable solvents are distilled water and organic solvents, like acetonitrile (ACN) or methanol. By providing liquid-tight prefilled liquid cartridges, partially harmful solvent vapors are avoided as well, because the prefilled liquid cartridge is formed completely liquid-tight outwardly. In the case of tipping of such liquid containers a contamination with liquid or gaseous ingredient is avoided as well, wherein the operation safety for a user can be increased significantly.

According to an embodiment, the liquid cartridge can be adapted to make a refilling of the liquid cartridge with liquid impossible. For example the liquid removal access can be configured to be irreversibly destroyed or untight by a first creating of an access to the liquid inside the liquid container. The liquid removal access can be provided with a one-way valve as well which allows a removal of liquid from the liquid container but not a filling of liquid into the liquid container. According to this design the prefilled liquid cartridge can thus be equipped with a mechanism which avoids that liquid cartridges are refilled with contaminated or not sterile liquids for example, which can negatively influence the reproducibility of measurements and the quality of the separation process and the efficiency of the separation process respectively. For example, a membrane which before seals the prefilled liquid cartridge in a fluid-tight manner can be irreversibly destroyed by the penetration of a removing lancet and/or the end of a fluid conduit of the sample separation device respectively. By a corresponding tearing of a membrane or foil, it can be avoided that an unauthorized or even dangerous refilling is carried out.

According to an alternative embodiment, the prefilled liquid cartridge can be designed as a refillable liquid cartridge by introducing a reversible sealing as a fluidic interface for removing the fluidic liquid, for example a rubber ring with a central bore of small dimension which can be pierced with a lancet or the like but is retightable.

According to an embodiment, the liquid removal access can be formed at the lower end of a side wall of the liquid container. Particularly it can be positioned (for example directly) adjacent to a bottom of the liquid cartridge. The providing of the liquid removal access at a side wall of the liquid container allows to form this at the upper side or the lower side free from fluidic accesses. Thereby the lower side can be designed for the stable setting up on a ground and the upper side with means for inserting the liquid cartridge into a form-fitting accommodation slot. Preferably, the removal of the liquid is carried out in a lower area of the liquid cartridge, because in this case the gravitational force acting on the liquid which is still contained in the cartridge is conveying the removal of liquid without applying a high suction pressure as well.

According to an embodiment, the liquid removal access can be formed fluid-tight and further so that it allows a fluid connection between the prefilled liquid and the at least one liquid conduit of the sample separation device only when piercing through a liquid cartridge access of the sample separation device. Particularly the liquid removal access can comprise a membrane, which is in principle fluid-tight but pierceable by a lancet or the like for forming an external access to liquid in the liquid container. According to an embodiment the liquid cartridge access can comprise a piercing equipment which is adapted for piercing of a pierceable fluid sealing of the liquid removal access for forming a fluid connection between the prefilled fluid and the at least one liquid conduit of the sample separation device when the liquid cartridge is inserted into the liquid cartridge accommodation. Just by sliding the prefilled liquid cartridge into an accommodation of the sample separation device, a fluidic coupling can be established. Thereby an untrained user can handle the prefilled liquid cartridge unproblematically and error-robust as well, because an intuitively sliding in is sufficient to enable the liquid supply. Further the handling of tubes or the like by a user is widely or completely disposable due to this design.

According to an embodiment, the liquid container can be formed from a rigid (for example shock-proof as well) solid state material and the liquid removal access can be provided with a fluid-tight pierceable membrane in the rigid solid state material (particularly fully surrounded by it). The rigid solid state material can be glass or plexiglass or another plastic. In this rigid container the pierceable membrane from a plastic or metal film material for example can be embedded then.

According to an embodiment, the liquid cartridge can comprise an identification feature (for example a radio-frequency identification (RFID)-Tag) indicative of the identity of the liquid cartridge which is formed to be identifiable by the sample separation device for identifying the liquid cartridge just in the case when the liquid cartridge is inserted in the liquid cartridge accommodation of the sample separation device. According to an embodiment, the sample separation device respectively can comprise an identification feature detecting equipment (for example an RFID-reader device) which is adapted to detect an identification feature indicative of the identity of the accommodated liquid cartridge, when the liquid cartridge is inserted in the liquid cartridge accommodation. Such an identification feature can for example be an RFID-Tag which can be readable by a corresponding reader device. In this way, information about the liquid in the liquid container, required for the sample separation can be exchanged, for example the kind of the fluid, a fluid volume, a purity grade, a date of expiry and other data. Alternatively to an RFID-Tag, other identification features are possible as well, for example a two-dimensional barcode, a three-dimensional barcode, alphanumeric characters or a magnetically stored information. Preferably the cartridge can be formed in the relation to the sample separation device so that a data communication between the sample separation device and the liquid cartridge, which allows the reading of the data, is only enabled in the inserted state. For example the sensing range of a corresponding sensor or reader device can be adapted accordingly.

According to an embodiment, the liquid cartridge can comprise a locking mechanism which is adapted for automatically locking at the sample separation device, when the liquid cartridge is inserted in the liquid cartridge accommodation of the sample separation device. According to an embodiment, the sample separation device can comprise a respective locking mechanism which is adapted for automatically locking at the liquid cartridge when the liquid cartridge is inserted in the liquid cartridge accommodation. Such a locking, for example by an interaction of such locking mechanisms, can be of a mechanical nature, for example two locking elements engaged with each other at the liquid cartridge and the sample separation device. Alternatively other locking elements are possible as well, for example attracting permanent magnets at the liquid cartridge and sample separation device or other locking elements.

According to an embodiment the liquid cartridge can be formed light-protected in the green wavelength range to thereby protect the prefilled fluid in the liquid container from ambient light in the green wavelength range. Such a light protection of the liquid container can ensure that an algae growth can be suppressed efficiently as well when a longer storing takes place. Algae require light in the green wavelength range for their growth. In this way the life period of the prefilled liquid cartridge can be clearly increased.

According to an embodiment, the liquid cartridge can comprise a particularly vertical (or slanted) sight slot for determining (for example for sensory determining by a sensor or for visually determining by a user) a filling level of the prefilled liquid and apart from that being formed opaque at least in the green wavelength range. According to this design, the liquid container can be formed from an optically non-transparent material apart from the preferably vertical sight slot, so that algae growth in the fluid is at least clearly inhibited. Alternatively a mere tinting of this area of the liquid container is possible as well. By the sight slot the filling level of the liquid cartridge can be read in an optical way. As an alternative to such a sight slot the filling level measurement can indeed be carried out by a weight determination of the liquid cartridge as well.

According to an embodiment, the liquid container can be formed from a tinted light protection material selectively absorbing light in the green wavelength range to protect the prefilled fluid in the liquid container from ambient light in at least the green wavelength range. A tinting, for example a brown tinting, of the complete liquid container can accomplish a corresponding filtering of green wavelength ranges of light which are required for algae growth. Because a tinting still allows a certain transparency of light, nothing is opposed to this optical filling level measurement.

According to an embodiment, a liquid capacity volume of the liquid container can be separated into multiple compartments which are filled with (same or different) liquids separated from each other. The liquid removal access can be adapted so that liquid from one (or more) of the compartments is provideable to the at least one liquid conduit selectively. According to this design, different fluids can be stored in one and the same prefilled liquid cartridge. For example, all operating liquids required for a certain chromatographic separation process, can be stored in different compartments of the liquid container which can be fluidically separated from each other for example by partition walls. Thereby a chromatographic gradient run can be performed exclusively by using operating liquids from the prefilled cartridge for example. Thus, a user just has to handle one single liquid cartridge to be able to execute a complete chromatographic separation process.

According to an embodiment, the liquid cartridge accommodation can comprise an insertion slot in the housing, which is adapted for the guided sliding of the liquid cartridge into the sample separation device so that the fluidic coupling between the at least one liquid conduit and the prefilled liquid is formed only by the guided sliding-in. By such an insertion slot it can be shown to a user in an intuitive way, at which position a prefilled liquid cartridge has to be inserted into a sample separation device to enable the correct connection of the fluid supply. A shape feature of the prefilled liquid cartridge can be adapted to a shape feature of the accommodation slot, so that a false inserting is made mechanically impossible.

According to an embodiment, a plurality of liquid cartridge accommodations (with separate liquid removal connections and piercing mechanisms respectively) can be provided at and/or in the at least one housing, wherein each of the liquid cartridge accommodations is adapted for accommodating and fluidic coupling of a corresponding prefilled liquid cartridge. By providing multiple liquid cartridge accommodations in a sample separation device, a redundant providing of multiple cartridges of the same liquids or different cartridges (for example with regard to filling volume and/or filling liquid) is possible as well. Thereby complex separation processes can be performed using different operating liquids and a sample separation experiment can be performed uninterrupted, as well when draining a liquid cartridge, because then it can be resorted to another cartridge.

According to an embodiment, the sample separation device or system can comprise a rest filling determination unit which is adapted to detect when a rest filling of a liquid cartridge accommodated in the liquid cartridge accommodation has fallen below a threshold value and triggers a predetermined event in this case. For example a filling level sensor can determine that a cartridge with respect to its filling level has fallen below a predetermined threshold value, for example 20% rest filling. When this event occurs, the liquid supply can then be changed to another cartridge of the same solvent. Thereby the rest period of such a sample separation device can be reduced. Such a filling level measurement can be executed by a weight measurement of the liquid cartridge in operation and inserted into an insertion slot, or by optical determining of the current filling level.

According to an embodiment, the triggered event can be outputting of a warning, switching a liquid supply of the fluid processing device from the liquid cartridge to another liquid cartridge or termination of a sample separation procedure. Other events can be triggered as well when falling below a minimum amount.

According to an embodiment, the sample separation device or system can be adapted as a plurality of fluidically coupled modules of which each is external defined by a separate housing and of which each comprises a functional equipment for providing a function within the scope of separating of components of the fluidic sample. Between such modules which are tower-like placeable on top of each other, an exchange of the operating liquids, a sample liquid, etc. can be carried out by tube connections. Each of these modules can be provided in a separate container, wherein each of the modules can inherit a partial function in the scope of the separation process. For example, the liquid supply of the single modules can be carried out by a separate and commonly used module for accommodation of the liquid cartridge(s). Alternatively, a liquid cartridge can be inserted into a module which fulfills a determined function in the scope of the separation procedure as well. For example at a modular liquid chromatography system, a pump module can be equipped with liquid cartridges as well to keep the fluidic transport paths for the supply of the pump with solvents short.

According to an embodiment, the sample separation device can comprise a control unit (for example a processor) which is adapted to control a sample separation procedure based on the identification of the accommodated liquid cartridge. According to a provided solvent, a chromatographic gradient run can be adapted accordingly.

According to an embodiment the sample separation device or system can be formed as a liquid chromatography separation device or system. Other sample separation methods, for example electrophoresis, are possible as well. The sample separation device can be a microfluidic measurement device, a life science device, a liquid chromatography device, an HPLC (High Performance Liquid Chromatography), a gas chromatography device, an electrophoresis device and/or a gel electrophoresis device. Indeed many other applications are possible.

According to an embodiment, in the method a separating of components of the fluidic sample can further be carried out by at least one functional equipment using the liquid conveyed from the liquid cartridge. For example, in the scope of a liquid chromatographic separation method, a gradient run or an isocratic run can be executed by the operating liquids of the prefilled cartridge.

The sample separation device or system can comprise a pump for moving a mobile phase. Such a pump can for example be adapted to pump the mobile phase through the system with a high pressure, for example some 100 bar up to 1000 bar and more. Alternatively or additionally, the sample separation device can comprise a sample injector for injection of the sample into a mobile phase. Such a sample injector can comprise a needle in a seat of an according fluid path, which can be extended from this seat to receive sample and which injects the sample in the system after reinserting in the seat. Alternatively or additionally the sample separation device can comprise a sample fractioner for fractioning of the separated components. Such a fractioner can guide the different components in different liquid containers for example. The analyzed sample can be guided to a waste container as well.

BRIEF DESCRIPTION OF FIGURES

Other objectives and many of the accompanying advantages of embodiments of the present invention will be easy observable and more intelligible with reference to the following detailed description of embodiments in accordance with the attached figures. Features which are functionally equal or similar will be provided with the same reference signs.

The illustration of the figures is schematic.

Figure 1:
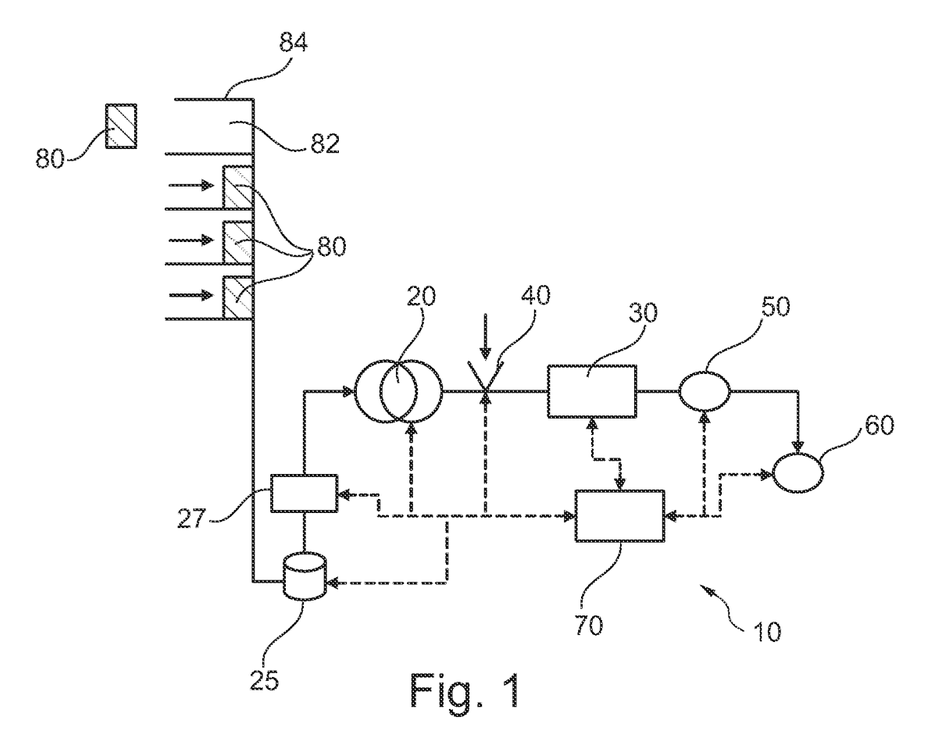
FIG. 1 shows an HPLC system according to an exemplary embodiment of the invention.

FIG. 1 shows the principle structure of an HPLC system 10, like it can be used in liquid chromatography. A pump 20 which is supplied with solvents from a supply unit 25 drives a mobile phase through a fluid separation device or unit 30 (like a chromatographic column for example) that includes a stationary phase. A degasser 27 can degas the solvents before they are delivered to the pump 20. A sample injection unit 40 is arranged between the pump 20 and the separation device 30 to introduce a sample liquid in the mobile phase. The stationary phase of the separation device 30 is provided to separate components of the sample liquid. A detector, see flow cell 50, detects separated components of the sample and a fractioner 60 can be provided to output separated components of the sample liquid, for example in containers provided for this, or in a drainage.

While a liquid path between the pump 20 and the separation device 30 is typically under high pressure, the sample liquid will be initially introduced at standard pressure in an area separated from the liquid path, a so-called sample loop of the sample unit 40 which then in turn introduces the sample fluid in the liquid path being under high pressure. When connecting the sample fluid initially under standard pressure in the sample loop in the liquid path under high pressure, the content of the sample loop will be brought to the system pressure of the HPLC system 10 suddenly (typically in the range of milliseconds).

A control unit 70 controls the individual modules 20, 27, 30, 40, 50, 60 of the sample separation device 10.

For a chromatographic separation device it is required that multiple different solvents are delivered by the supply unit 25. Like indicated schematically in FIG. 1, therefore different prefilled liquid cartridges 80 can be inserted into corresponding insertion slots 82 of a cartridge accommodation equipment 84. For each solvent the pump 20 requires during operation, one or more liquid cartridges 80 can be provided.

Figure 2:
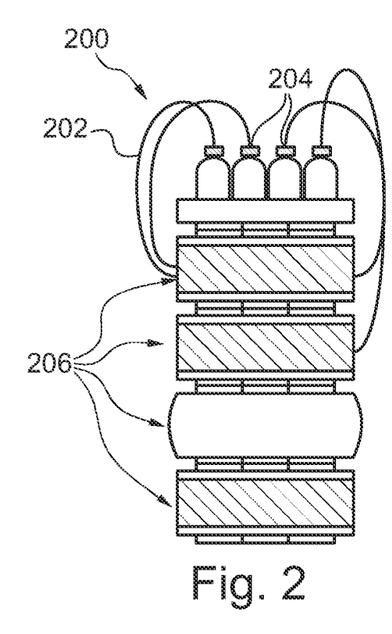
FIG. 2 shows a sample separation device or system with a conventional liquid supply.

FIG. 2 shows a conventional method for supplying different modules 206 of a sample separation device 200 with operating liquids. For that, individual bottles 204 are placed on a top side of the modular tower and are connected to the liquid acceptors in the modules 206 of the sample separation device 200 by tube connections 202. This on the one hand requires a handling of bottles 204 above shoulder height, which can cause a tipping of the bottles 204 and thereby a contamination of the user or the sample separation device 200 with partially harmful liquids. The tube connections 202 can crease or fail otherwise as well, so that reliability of the liquid supply of the individual modules 206 of the sample separation device 200 cannot always be ensured.

Figure 3:
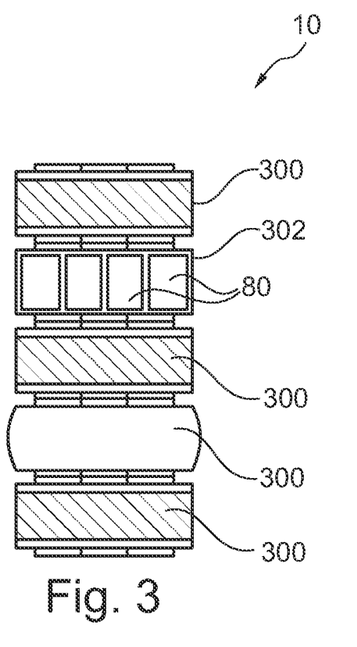
FIG. 3 shows a sample separation device or system with a liquid supply in the form of prefilled liquid cartridges according to an exemplary embodiment of the invention.

In contrast to FIG. 2, FIG. 3 shows a sample separation device or system 10 according to an exemplary embodiment of the invention. In this case different modules 300 are shown as well which are tower-like arranged on the top of each other in a modular operating mode. The individual modules 300 can be designed like the components 20, 27, 30, 40, 50, 60 according to FIG. 1. A separate module with a housing 302 is provided to provide insertion slots in which the individual prefilled liquid cartridges 80 can be accommodated. A user only has to slide them in these insertion slots in a desired manner to form a fluidic connection. Tubes lying around, free-standing bottles or the like are avoided as well as the requirement of handling bottles above shoulder height. By the fluid-tight forming of the prefilled liquid cartridges 80, an undesired leakage of vapors or liquids is avoided as well. The handling of the liquid cartridges 80 is easy, because it is already visually shown to a user by the form adaption of the liquid cartridges 80 to the insertion slots of the module for accommodating the liquid cartridges 80.

Figure 4:
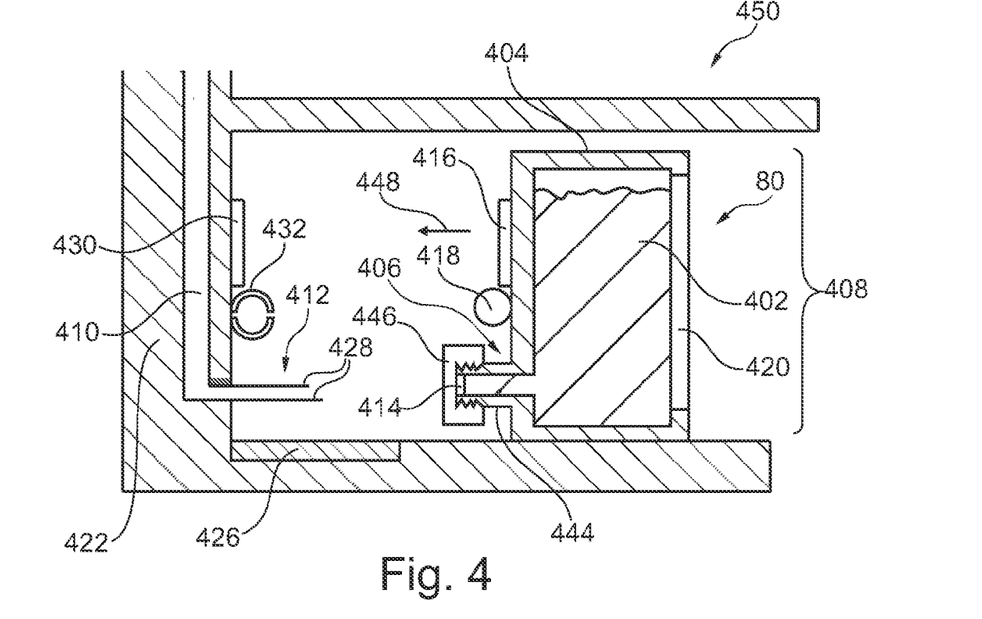
FIG. 4 shows a cross-sectional view of a module with a prefilled liquid cartridge for a chromatographic sample separation device or system according to an exemplary embodiment of the invention.

FIG. 4 shows an arrangement 450 of a just partially shown sample separation device or system (which can contain the components according to FIG. 1) and a prefilled liquid cartridge 80 for providing an operating liquid according to an exemplary embodiment of the invention. Further, not shown liquid cartridges 80 for providing further operating liquids can be provided.

The sample separation device comprises container walls 422 in which the fluid conduits 410 are integrated. Lying around or unsorted tubes can be avoided by the wall integration. The prefilled liquid cartridge 80 shown in FIG. 4 is provided for fluidic coupling to the liquid conduits 410 of the sample separation device to use liquid 402 contained in it as operating liquid for sample separation in the connected state. At separating of components of a fluidic sample, for example a biological sample, the liquid 402 which is contained inside a liquid container 404 of the prefilled liquid cartridge 80 is used for example for a gradient run of a chromatographic experiment. FIG. 4 further shows that a liquid removal access 406 is provided in the lower side wall area. This is formed fluid-tight by a pierceable membrane 414. This membrane 414 is attached at a docking connection 444 which has an external thread. By this external thread a cover 446 supplied with a corresponding internal thread can be screwed on the prefilled liquid cartridge 80.

For removal of liquid 402 for providing as operating liquid for the sample separation device, it is sufficient that a user unscrews the cover 446 and inserts the liquid cartridge 80 in the insertion slot 408 in a manner shown in FIG. 4 along an arrow 448 shown there. A liquid cartridge terminal 412 is provided and connected respectively to the end of the liquid conduit 410 and has a lancet 428 for piercing the membrane 414 when the liquid cartridge 80 is slided-in along the arrow direction 448. Thereby a fluid connection between the inside of the liquid container 404 and the liquid conduit 410 is formed so that the liquid 402 is successively sucked from the liquid container 404, pumped through the liquid conduit 410 and delivered to desired components of the sample separation device.

To suppress algae growth in the liquid 402 the liquid container 404 is manufactured from a optically non-transparent or at least brown tinted material (for example an adequate plastic) to avoid that respective wavelengths of the ambient light stimulate such an algae growth. The filling level of the liquid 402 in the liquid container 404 can indeed be determined, for example by a weight determination equipment 426 which can determine a respective rest weight of the liquid cartridge 80 during the operation. Alternatively the filling level can be determined optically by an optical transparent vertical sight slot 420 in the liquid container 404 so that the current filling level and hence the rest filling can be determined continuously. When determined that the remaining filling level is not sufficient to finish the experiment, the liquid supply can for example be switched to another liquid cartridge 80 inserted in the sample separation device or the measurement can be interrupted or terminated. Outputting an alarm message or an error message is possible as well.

By the inserting not only is the establishment of a fluid communication between the inside of the container and the liquid conduit 410 achieved, but simultaneously the establishing of a communication connection between an identification feature 416, for example an RFID-Tag, at the prefilled liquid cartridge 80 on the one hand and a reader device 430, for example an RFID reader device, of the sample separation device is achieved. When both components 416, 430 are in communication range with each other, thus the sample separation device can read information about the prefilled liquid cartridge 80, for example the kind of liquid contained therein, the liquid volume, a date of expiry etc. This information can be used for the control of the sample separation device.

To give a user a haptic feedback for acknowledgement of the correct inserting of the prefilled liquid cartridge 80 in the accommodation slot 408, corresponding mechanical latching elements 432 of the sample separation device and the prefilled liquid cartridge 80 latch with each other when the prefilled liquid cartridge 80 is inserted correctly in the accommodation slot 408. When the prefilled liquid cartridge 80 is empty, the user can disconnect the latching connection by exerting a drag force and take out the liquid cartridge 80 from the insertion slot 408.

Figure 5:
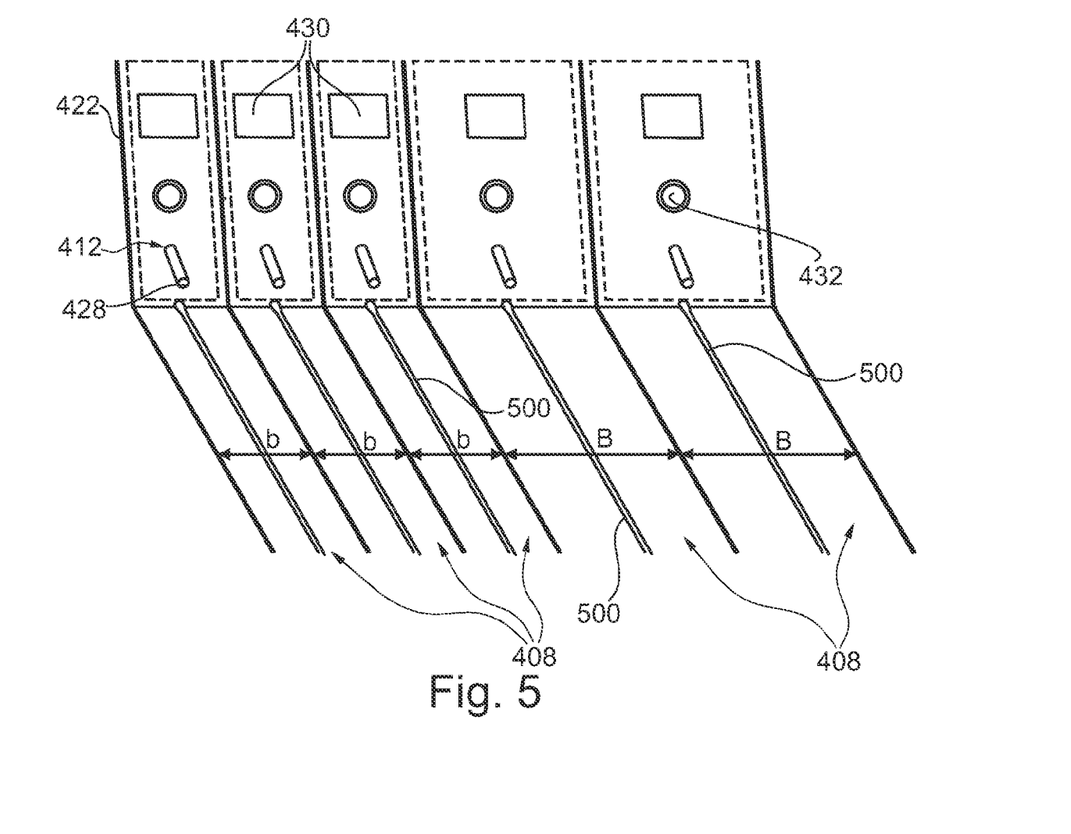
FIG. 5 shows plural insertion slots for inserting and simultaneously handling plural liquid cartridges for a sample separation device or system according to an exemplary embodiment of the invention.

FIG. 5 shows that multiple accommodation slots 408 can be provided for multiple liquid cartridges 80 in a module of the sample separation device or system and in the entire sample separation device or system respectively. Along respective guide rails 500 the respective liquid cartridge 80 which can comprise a corresponding guide groove in its bottom area can be slid-in and then latched by forming a mechanical latching connection between components 418 and 432. By the protruding lancet 428 which pierces a membrane 414 of the respective prefilled liquid cartridge 80, the fluid connection can be established. FIG. 5 also shows that reader devices can be provided for each accommodation slot.

The different accommodation slots 408 in FIG. 5 can comprise different but standardized sizes. In the shown example, accommodation slots 408 for accommodation of liquid cartridges 80 of the width B and the width b are shown, wherein B>b.

It should be observed that the term "comprise" does not exclude other elements and that the term "one" does not exclude a plurality. Elements which are described in the context of different embodiments, can also be combined. It should be observed also that reference signs in the claims should not be interpreted as restrictive to the scope of protection of the claims.

The invention claimed is:
1. A sample separation system, comprising:
at least one housing;
at least one fluid separation device disposed at least partially in the at least one housing and configured for separating components of a fluidic sample by chromatography or electrophoresis using liquid of a prefilled liquid cartridge;

at least one liquid conduit disposed at the at least one housing and configured for supplying the fluid separation device with liquid; and a liquid cartridge accommodation disposed at the at least one housing, the liquid cartridge accommodation configured for receiving a corresponding prefilled liquid cartridge and forming a fluidic coupling between the at least one liquid conduit and a liquid removal access of the prefilled liquid cartridge, in response to the prefilled liquid cartridge being inserted in the liquid cartridge accommodation.

2. A sample separation system according to claim 1, wherein the liquid cartridge accommodation comprises an insertion slot in the at least one housing, and the insertion slot is configured for guiding insertion of the prefilled liquid cartridge into the liquid cartridge accommodation, such that the fluidic coupling is formed in response to guiding the insertion.

3. A sample separation system according to claim 1, comprising a plurality of liquid cartridge accommodations disposed at the at least one housing, wherein each of the liquid cartridge accommodations is configured for receiving a corresponding prefilled liquid cartridge.

4. A sample separation system according to claim 1, comprising a rest filling determination unit configured for detecting when a rest filling of a prefilled liquid cartridge inserted in the liquid cartridge accommodation has fallen below a predetermined threshold value and, in response to the detecting, triggering a predetermined event.

5. A sample separation system according to claim 4, wherein the predetermined event is selected from the group consisting of: an outputting of a warning, a switching of a liquid supply of the sample separation system from the prefilled liquid cartridge to another prefilled liquid cartridge, and a finishing of a sample separation procedure.

6. A sample separation system according to claim 1, wherein the liquid cartridge accommodation comprises a piercing mechanism configured for piercing a fluid seal of the liquid removal access to form the fluidic coupling, when the prefilled liquid cartridge is inserted into the liquid cartridge accommodation.

7. A sample separation system according to claim 1, wherein the at one least housing comprises a first housing and a second housing, and further comprising a plurality of separate, fluid coupled modules, the plurality of separate, fluid coupled modules comprising a first module comprising a first housing and a second module comprising a second housing, wherein the at least one fluid separation device is disposed at the first housing, and the liquid cartridge accommodation is disposed at the second housing.

8. A sample separation system according to claim 1, comprising an identification feature detecting device configured to detect an identification feature indicative of the identity of the prefilled liquid cartridge, when the prefilled liquid cartridge is inserted in the liquid cartridge accommodation.

9. A sample separation system according to claim 8, comprising a control unit configured to control a sample separating procedure based on the identification of the inserted prefilled liquid cartridge.

10. A sample separation system according to claim 1, comprising a locking component configured for automatically locking the prefilled liquid cartridge into engagement with the liquid cartridge accommodation, when the prefilled liquid cartridge is inserted in the liquid cartridge accommodation.

11. A sample separation system according to claim 1, wherein the fluid separation device comprises a liquid chromatography column.

12. An arrangement, comprising:
the sample separation system according to claim 1; and
a prefilled liquid cartridge configured to be inserted in the liquid cartridge accommodation for fluidly connecting to the at least one liquid conduit.

13. An arrangement according to claim 12, wherein the prefilled liquid cartridge comprises:
a liquid container prefilled with liquid; and
a liquid removal access communicating with the liquid container, the liquid removal access configured to be fluidically coupled to the at least one liquid conduit by inserting the liquid cartridge in the corresponding liquid cartridge accommodation.

14. An arrangement according to claim 13, wherein the liquid container is prefilled with the liquid in a fluid-tight manner before a first liquid removal through the liquid removal access.

15. An arrangement according to claim 13, wherein the liquid container is prefilled with a solvent.

16. An arrangement according to claim 13, wherein the prefilled liquid cartridge is configured to make a refilling of the liquid container with liquid impossible.

17. An arrangement according to claim 13, wherein the liquid container comprises a side wall, the side wall comprises a lower end, and the liquid removal access is disposed at the lower end.

18. An arrangement according to claim 13, wherein the liquid removal access is fluid-tight and is further configured to allow a fluid connection between the liquid container and the at least one liquid conduit only upon piercing through the liquid removal access.

19. An arrangement according to claim 13, wherein the at least one liquid conduit communicates with a lancet, the liquid container is formed from a rigid solid material, and the liquid removal access comprises a fluid-tight pierceable membrane configured for being pierced by the lancet in a fluid-tight manner, when the prefilled liquid cartridge is inserted in the liquid cartridge accommodation.

20. An arrangement according to claim 13, wherein the prefilled liquid cartridge comprises an identification feature indicative of the identity of the prefilled liquid cartridge.

21. An arrangement according to claim 13, comprising a locking component configured for automatically locking the prefilled liquid cartridge into engagement with the liquid cartridge accommodation, when the prefilled liquid cartridge is inserted in the liquid cartridge accommodation.

22. An arrangement according to claim 13, wherein the liquid container is formed light-protected in the green wavelength range to thereby protect the prefilled liquid in the liquid container from ambient light in the green wavelength range.

23. An arrangement according to claim 22, wherein the liquid container comprises a sight slot for determining a filling level of the prefilled liquid and otherwise is formed opaque in at least the green wavelength range.

24. An arrangement according to claim 22, wherein the liquid container is formed from a tinted light-protection material absorbing light of a green wavelength range selectively to protect the prefilled fluid in the liquid container from ambient light at least in the green wavelength range.

25. An arrangement according to claim 13, wherein the liquid container comprises a fluid accommodation volume separated into a plurality of compartments filled with liquid separately from each other, and the liquid removal access is configured to selectively provide liquid to the at least one liquid conduit from a selected one of the compartments.

26. A method of supplying a sample separation system with liquid for separating of components of a fluidic sample, the method comprising:
   inserting a prefilled liquid cartridge prefilled with liquid in a liquid cartridge accommodation at at least one housing of the sample separation system so that, by the inserting, a fluidic coupling between at least one liquid conduit of the sample separation system and a liquid container of the prefilled liquid cartridge is formed by a liquid removal access of the liquid container; and
   conveying the liquid from the inserted prefilled liquid cartridge through the liquid removal access and the at least one liquid conduit to a fluid separation device of the sample separation system, wherein the fluid separation device is disposed at least partially in the at least one housing and is configured for separating components of the fluidic sample by chromatography or electrophoresis using liquid of the prefilled liquid cartridge.

27. A method according to claim 26, further comprising operating the sample separation system to separate components of the fluidic sample at the fluid separation device by chromatography or electrophoresis, using the liquid conveyed from the prefilled liquid cartridge.

* * * * *